United States Patent
Massarwa et al.

(10) Patent No.: US 12,070,277 B2
(45) Date of Patent: Aug. 27, 2024

(54) REGIONAL RESOLUTION IN FAST ANATOMICAL MAPPING

(71) Applicant: BIOSENSE WEBSTER (ISRAEL) LTD., Yokneam (IL)

(72) Inventors: Fady Massarwa, Baka Al Gharbiyya (IL); Assaf Cohen, Kiryat Bialik (IL); Akram Zoabi, Haifa (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 706 days.

(21) Appl. No.: 17/123,624

(22) Filed: Dec. 16, 2020

(65) Prior Publication Data

US 2022/0183761 A1  Jun. 16, 2022

(51) Int. Cl.
| | |
|---|---|
| *A61B 34/30* | (2016.01) |
| *A61B 34/10* | (2016.01) |
| *A61B 34/20* | (2016.01) |
| *A61B 90/00* | (2016.01) |
| *G06T 17/20* | (2006.01) |

(52) U.S. Cl.
CPC ............. *A61B 34/20* (2016.02); *A61B 34/10* (2016.02); *A61B 90/361* (2016.02); *G06T 17/205* (2013.01); *A61B 2034/107* (2016.02); *G06T 2210/41* (2013.01)

(58) Field of Classification Search
CPC ......... A61B 34/30; A61B 34/20; A61B 34/10; A61B 19/201; A61B 19/203; A61B 19/5244; A61B 90/361; A61B 34/00
See application file for complete search history.

(56) References Cited

U.S. PATENT DOCUMENTS

| | | | |
|---|---|---|---|
| 5,391,199 A | 2/1995 | Ben Haim | |
| 6,239,724 B1 | 5/2001 | Doron | |
| 6,332,089 B1 * | 12/2001 | Acker | A61N 7/02 |
| | | | 128/899 |
| 6,484,118 B1 | 11/2002 | Govari | |
| 6,618,612 B1 | 9/2003 | Acker | |
| 6,690,963 B2 | 2/2004 | Ben Haim | |
| 9,014,795 B1 | 4/2015 | Yang | |
| 10,902,679 B2 | 1/2021 | Molyneaux | |
| 2002/0065455 A1 | 5/2002 | Ben Haim | |
| 2003/0120150 A1 | 6/2003 | Govari | |

(Continued)

FOREIGN PATENT DOCUMENTS

| | | |
|---|---|---|
| JP | 2020075132 A | 5/2020 |
| WO | WO1996005768 A1 | 2/1996 |

OTHER PUBLICATIONS

European Search Report for corresponding EPA No. 21214605.4 dated May 25, 2022.

*Primary Examiner* — Vi X Nguyen

(57) ABSTRACT

A method includes, receiving, on a surface of an anatomical map of a patient organ having a first presentation, a selection of a first selected region, which is intended to have a second presentation, different from the first presentation. A perimeter of the first selected region, and at least an unselected area positioned within the first selected region, are identified. A second selected region is produced, the second selected region includes the first selected region and the unselected area. The anatomical map, having the second presentation applied to the second selected region, is displayed.

8 Claims, 3 Drawing Sheets

(56) References Cited

U.S. PATENT DOCUMENTS

| | | |
|---|---|---|
| 2004/0068178 A1 | 4/2004 | Govari |
| 2010/0317962 A1* | 12/2010 | Jenkins ................. A61B 5/062 |
| | | 600/411 |
| 2015/0196214 A1 | 7/2015 | Shuros |
| 2015/0257671 A1 | 9/2015 | Laughner |
| 2015/0366476 A1 | 12/2015 | Laughner |
| 2018/0296108 A1 | 10/2018 | Stewart |

* cited by examiner

REGIONAL RESOLUTION IN FAST ANATOMICAL MAPPING

FIELD OF THE INVENTION

The present invention relates generally to medical devices, and particularly to methods and systems for improving regional resolution in fast anatomical mapping.

BACKGROUND OF THE INVENTION

Various techniques for presenting information on anatomical maps have been published.

For example, U.S. Patent Application Publication No. 2015/0196214 describes a catheter shaft with a plurality of electrodes coupled thereto and a processor coupled to the catheter shaft. The processor may be capable of collecting a set of signals from the plurality of electrodes, characterizing the set of signals, generating a visual representation of the set of signals and refining the visual representation.

U.S. Patent Application Publication No. 2015/0366476 describes medical devices and methods for making and using medical devices. An example medical device may include a system for mapping the electrical activity of the heart. The system may include a catheter shaft with a plurality of electrodes. The system may also include a processor. The processor may be capable of collecting a set of signals from at least one of the plurality of electrodes. The set of signals may be collected over a time period. The processor may also be capable of calculating at least one propagation vector from the set of signals, generating a data set from the at least one propagation vector, generating a statistical distribution of the data set and generating a visual representation of the statistical distribution.

SUMMARY OF THE INVENTION

An embodiment of the present invention that is described herein provides a method, including receiving, on a surface of an anatomical map of a patient organ having a first presentation, a selection of a first selected region, which is intended to have a second presentation different from the first presentation. A perimeter of the first selected region, and at least an unselected area positioned within the first selected region, are identified. A second selected region is produced, the second selected region includes the first selected region, and the unselected area. The anatomical map, having the second presentation applied to the second selected region, is displayed.

In some embodiments, the first presentation includes a first mapping resolution of the anatomical map and the second presentation includes a second mapping resolution of the second selected region of the anatomical map. In other embodiments, the first selected region includes one or more selected areas and at least the unselected area, and identifying the unselected area includes identifying, within the first selected region, at least an isolated unselected area surrounded by the one or more selected areas. In yet other embodiments, the anatomical map includes a mesh of polygons, and producing the second selected region includes, selecting one or more unselected polygons within the isolated unselected area.

In an embodiment, selecting the one or more unselected polygons includes, applying a flood fill algorithm to the unselected polygons within the isolated unselected area. In another embodiment, at least one of the polygons of the anatomical map includes a triangle. In yet another embodiment, the first selected region includes first and second selected areas at least partially disjoint from one another by the unselected area, and identifying the unselected area includes identifying, within the first selected region, the unselected area that is partially enclosed by the first and second selected areas.

In some embodiments, the anatomical map includes a mesh of polygons, the first selected area includes first polygons and the second selected area includes second polygons, the first and second selected areas are at least partially disjoint by unselected polygons of the unselected area, and producing the second selected region includes, (i) computing a distance between one or more pairs of the first and second polygons, and (ii) selecting a path of the unselected polygons located between any pair of the selected polygons, which is selected from the first and second polygons. In other embodiments, the path includes a geodesic path. In yet other embodiments, at least one of the polygons includes a triangle.

There is additionally provided, in accordance with an embodiment of the present invention, a system including a processor and an output device. The processor is configured to: (a) receive, on a surface of an anatomical map of a patient organ having a first presentation, a selection of a first selected region, which is intended to have a second presentation different from the first presentation; (b) identify (i) a perimeter of the first selected region, and (ii) at least an unselected area positioned within the first selected region; and (c) produce a second selected region, including (i) the first selected region, and (ii) the unselected area. The output device is configured to display the anatomical map having the second presentation applied to the second selected region.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
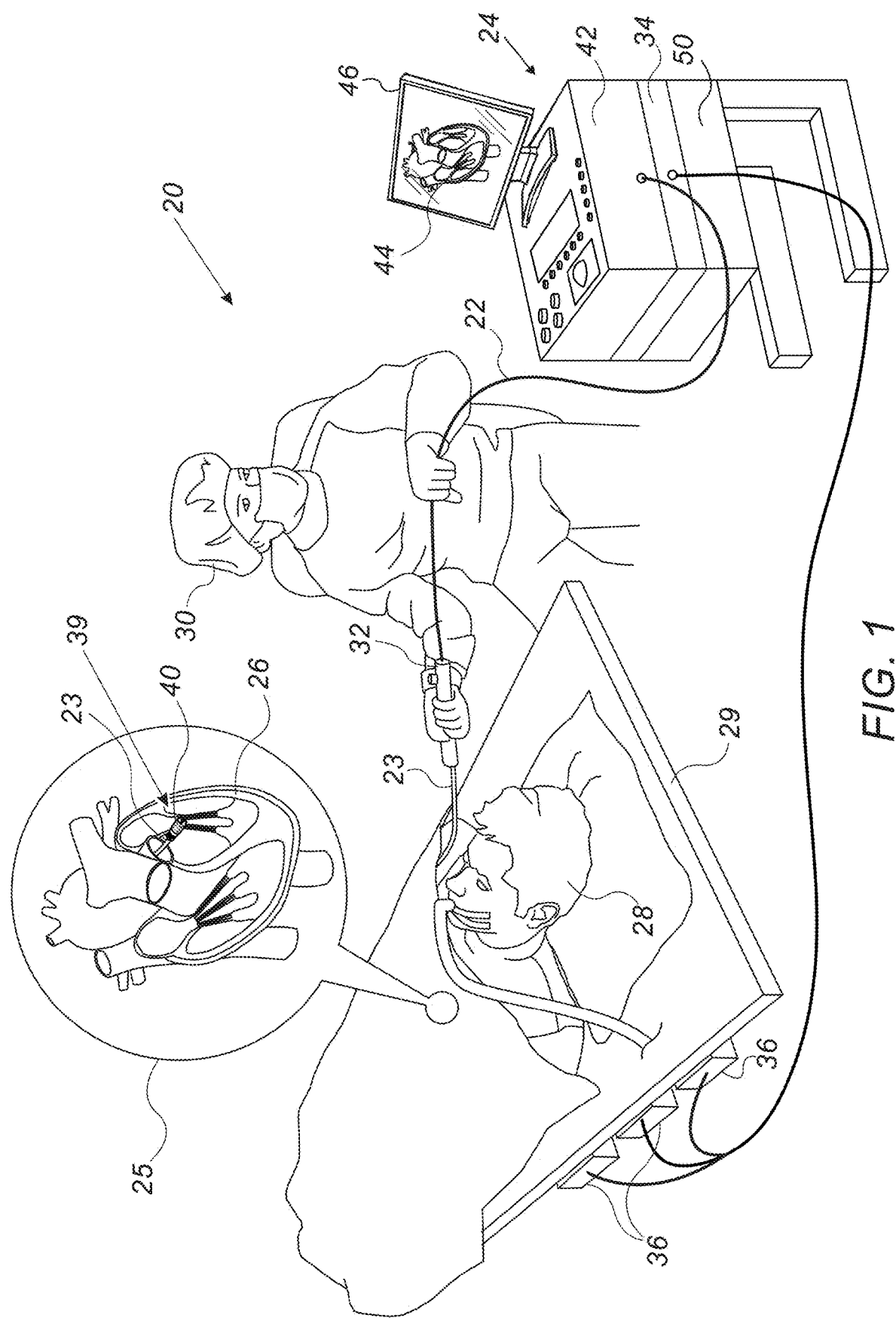
FIG. 1 is a schematic, pictorial illustration of a catheter-based position-tracking and ablation system, in accordance with an exemplary embodiment of the present invention.

Embodiments of the present invention that are described hereinbelow provide techniques for improving regional resolution in fast anatomical mapping (FAM) of a patient organ. For example, FAM of a patient heart may be used, inter alia, for planning an ablation procedure.

In some cases, a physician may select a region of interest, in an anatomical map of the patient heart, using any suitable selection tool, such as a brush that marks the region on the surface of the anatomical map that is captured by the brush shape on the screen. The selected region is intended to be presented using presentation parameters different from the presentation parameters of other section of the anatomical map. For example, when planning ablation of a given pulmonary vein (PV) at the heart atria, the physician may wish to have the given PV at high mapping resolution, and the other sections of the atria at low mapping resolution (i.e., smoothed or interpolated).

In some embodiments, the selected region, which is initially displayed in low mapping resolution, is replaced with a high resolution map of the same region, and displayed on the anatomical map.

In some cases, one or more areas within the region of interest may not be selectable by the brush. For example, at a given perspective, some anatomical areas in the region of interest may be hidden from the selection tool, e.g., due to the topographical structure of the region of interest. In such cases, the hidden areas will not be selected and will remain presented in low resolution, whereas the selected areas will be presented in high resolution. Such mixed resolution may result in presenting artifacts in the anatomical map and/or omitting essential sections in the region of interest. Therefore, when selecting a region of interest, it is important to select all the areas thereof.

In some embodiments, a system for improving the selection of areas in the region of interest comprises a processor and an output device, such as a display. The processor is configured to receive, on the surface of the anatomical map displayed in low mapping resolution, a selection of a first selected region, which is intended to be displayed using a higher mapping resolution.

In some embodiments, the processor is configured to identify, the perimeter of the first selected region, and at least one unselected area positioned within the perimeter of the first selected region. Note that the processor is configured to identify the perimeter even when the perimeter falls on one or more unselected areas. In some embodiments, when the perimeter falls on one or more unselected areas, the processor is configured to define the perimeter in the one or more unselected area(s) using any suitable technique. For example, by connecting (using a virtual line of the perimeter) between edges of two or more selected areas, which are positioned at the sides of the respective unselected area, and are falling on the perimeter.

In some embodiments, the areas of the anatomical map (and selected region) are calculated and displayed using a mesh of polygons, such as triangles. The processor is configured to check whether the one or more unselected area(s) are surrounded by the perimeter of the selected areas in the view of the brush selection tool. Additionally or alternatively, the processor is configured to check whether the one or more unselected areas are surrounded by triangles of the selected areas.

In case the selected area comprises one connected component, which may have one or more "holes" or openings, the processor is configured to "fill" the "holes" using any suitable technique. Additionally or alternatively, in case the unselected area is surrounded by the selected triangles, the processor is configured to apply any suitable algorithm for selecting the triangles within the unselected area. For example, the processor may apply a flood fill algorithm for "filling" the surrounded unselected area.

In case the unselected area is not surrounded, the processor is configured to calculate the distance of a path of unselected triangles located between any two selected triangles. In some embodiments, the processor is configured to select from among the calculated paths, a geodesic path of triangles for surrounding one or more sections within the unselected area. After selecting the triangles of the geodesic path, the processor checks whether all the unselected area is surrounded by the selected triangles described above, and repeats the formation of geodesic path and checking the perimeter until the unselected area has been surrounded by the selected triangles, meaning that the selected area forms a connected component. Subsequently, the processor selects all the triangles within the surrounded unselected area as described above.

The disclosed techniques improve the accuracy of regional resolution in anatomical mapping, by including unselected areas within the regions of interest.

System Description

FIG. 1 is a schematic, pictorial illustration of a catheter-based position-tracking and ablation system 20, in accordance with an embodiment of the present invention. In some embodiments, system 20 comprises a catheter 22, in the present example a cardiac catheter, and a control console 24. In the embodiment described herein, catheter may be used for any suitable therapeutic and/or diagnostic purposes, such as ablation of tissue in a heart 26 and/or for mapping cardiac arrhythmias by sensing intra-cardiac electrical signals.

In some embodiments, console 24 comprises a processor 42, typically a general-purpose computer, with suitable front end and interface circuits for exchanging signals with catheter 22 (e.g., receiving intra-cardiac electrical signals and applying ablation pulses to tissue of heart 26), and for controlling other components of system 20 described herein. Processor 42 may be programmed in software to carry out the functions that are used by the system, and is configured to store data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out using an application-specific integrated circuit (ASIC) or any suitable type of programmable digital hardware components.

Reference is now made to an inset 25. In some embodiments, catheter 22 comprises a distal-end assembly 40, and a shaft 23 for inserting distal-end assembly 40 to a target location for ablating tissue in heart 26. During an ablation procedure, physician 30 inserts catheter 22 through the vasculature system of a patient 28 lying on a table 29. Physician 30 moves distal-end assembly 40 to the target location in heart 26 using a manipulator 32 near a proximal end of catheter 22, which is connected to interface circuitry of processor 42.

In some embodiments, catheter 22 comprises a position sensor 39 of a position tracking system, which is coupled to the distal end of catheter 22, e.g., in close proximity to distal-end assembly 40. In the present example, position sensor 39 comprises a magnetic position sensor, but in other embodiments, any other suitable type of position sensor (e.g., other than magnetic-based) may be used.

Reference is now made back to the general view of FIG. 1. In some embodiments, during the navigation of distal-end assembly 40 in heart 26, processor 42 receives signals from magnetic position sensor 39 in response to magnetic fields from external field generators 36, for example, for the purpose of measuring the position of distal-end assembly 40 in heart 26. In some embodiments, console 24 comprises a driver circuit 34, configured to drive magnetic field generators 36. Magnetic field generators 36 are placed at known positions external to patient 28, e.g., below table 29.

In some embodiments, processor 42 is configured to display, e.g., on a display 46 of console 24 or on any other suitable output device, the tracked position of distal-end assembly 40 overlaid on an image 44 of heart 26. In some embodiments, processor 42 is configured to display an anatomical map (shown in FIG. 2 below) of at least part of heart 26, as will be described in detail in FIG. 2 below.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical systems.

Figure 2:
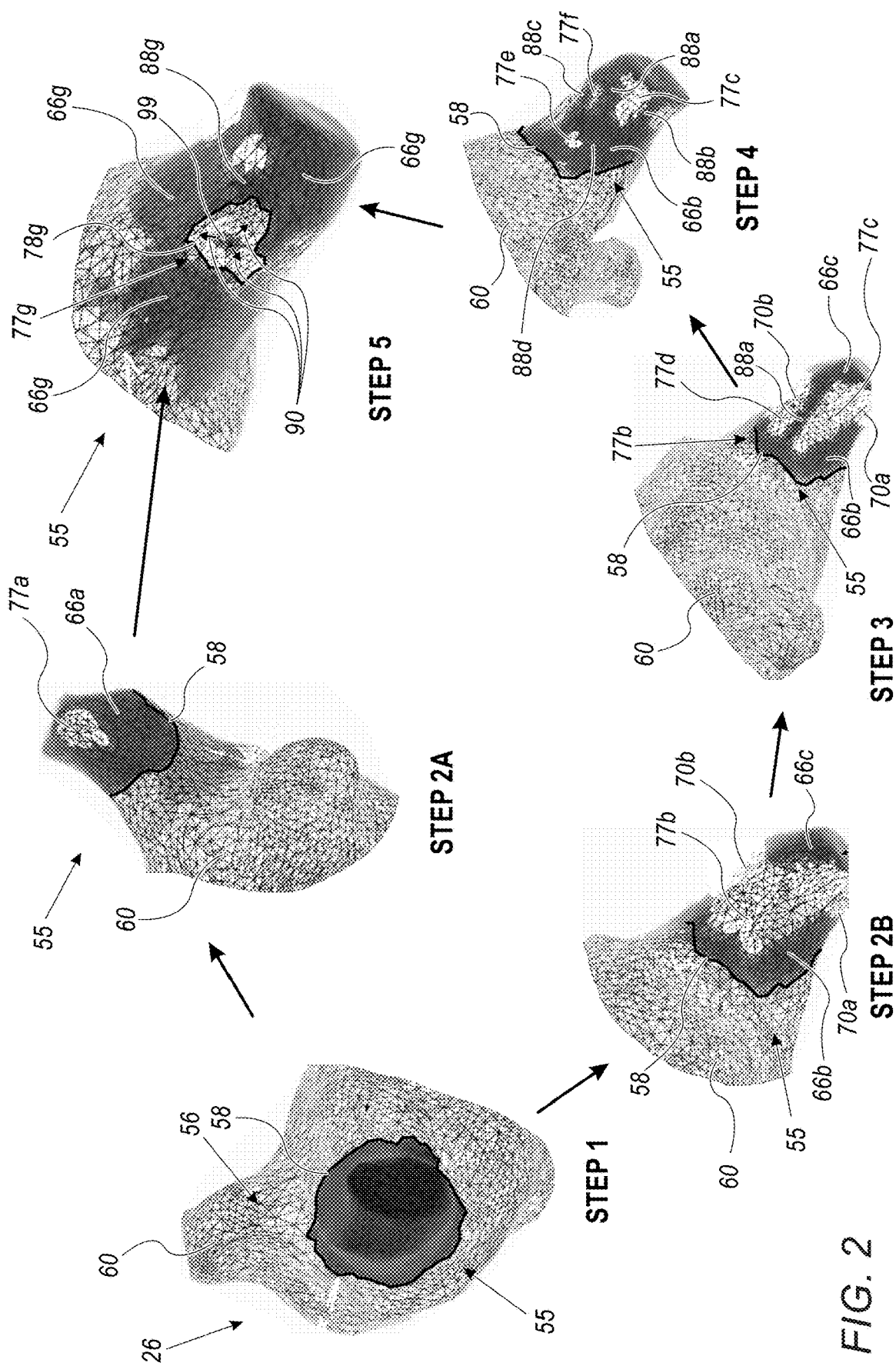
FIG. 2 is a diagram that schematically illustrates a method for improving a region selection process for displaying heart tissue in selected regional resolution, in accordance with an exemplary embodiment of the present invention.

Improving Region Selection Process for Displaying Heart Tissue in Selected Regional Resolution FIG. 2 is a diagram that schematically illustrates a method for improving a region selection process for displaying different regions of heart 26 in different selected regional resolution, in accordance with an embodiment of the present invention. In the context of the present disclosure and in the claims, the terms "resolution" and "mapping resolution" are used interchangeably and refer to the level of details displayed to physician 30, e.g., on display 46, in different regions of a map of heart 26, as will be described in detail herein.

The method begins at a step 1 with receiving a region 55, which is selected by physician 30 (or by any other user of system 20) on the surface of an anatomical map 60 of heart 26. Region 55 may be selected by physician 30 using any suitable selection tool, such as but not limited to a brush of the CARTO™ system described in FIG. 1 above.

In some embodiments, physician 30 controls system 20 to display anatomical map 60 in a first resolution and selected region 55 in a second resolution, different from the first resolution. In the present example, physician 30 plans an ablation in a pulmonary vein located within region 55, and therefore, controls system 20 to display region 55, which is the region of interest, in high resolution. In the context of the present disclosure and in the claims, the term "high resolution" refers to a polygon (described in detail below), which serves as a unit cell of the anatomical map, and has a size of about 2 mm or any other suitable size, for example, between about 1 mm and 5 mm. Moreover, physician 30 is less interested in the area of anatomical map 60, and therefore controls system 20 to display anatomical map 60 smoothed using low resolution (e.g., having the size of the aforementioned polygon between about 10 mm and 30 mm, in the present example, about 20 mm). In other words, processor 42 is configured to display different regions of the anatomical map in different resolutions, so as to provide physician 30 with sufficiently-high resolution at the regions of interest.

In the context of the present disclosure and in the claims, the terms "about" or "approximately" for any numerical values or ranges indicate a suitable dimensional tolerance that allows the part or collection of components to function for its intended purpose as described herein.

In some embodiments, processor 42 is configured to apply to the surface of anatomical map 60 and region 55, a mesh of polygons, in the present example a mesh of triangles 56. Each triangle serves as a cell for displaying information and/or for selecting an area within anatomical map 60 and region 55. In other words, the resolution of the information display and/or area selection is the size of triangle 56 of the mesh.

In an embodiment, the triangle size defines the resolution of display and/or area selection of anatomical map 60, and the size of the triangle is defined, in this example, by the maximal length of the triangle edges.

In other embodiments, processor 42 may apply to anatomical map 60 any other type of one or more polygons having any suitable size.

In some embodiments, region 55 has been selected by physician 30 so as to display a combined map of anatomical map 60 and region 55 in different resolutions. In such embodiments, processor 42 is configured to replace the selected region 55 having low resolution, with a higher resolution map of the same area covered by region 55.

Reference is now made to step 2A and 2B. In some cases the anatomical structure of heart 26 may have one or more areas within region 55, which are invisible during the selection of physician 30, and therefore are not selected during the selection made by physician 30. In some embodiments, as shown in step 2A and 2B, region 55 has one or more selected areas, such as an area 66a (in step 2A), and areas 66b and 66c (in step 2B), in which the triangles are selected and shown in a first color (filled with a gray color, in the example of FIG. 2). However, some areas within region 55, such as areas 77a (in step 2A) and 77b (in step 2B), were intended to be selected, but were not captured by the selection tool, for example, due to the anatomical structure of heart 26, or for any other reason. Areas 77a and 77b are referred to herein as unselected areas, and the triangles of areas 77a and 77b have the same filling color of other unselected triangles, e.g., areas out of perimeter 58 of region 55, which are filled with a white color in the example of FIG. 2.

Note that unselected areas in the steps of FIG. 2 have numerals 77a-77g and areas being selected during the selection of region 55 have numerals 66a, 66b and 66g, as will be described herein.

In some embodiments, at steps 2A and 2B, processor 42 is configured to identify perimeter 58, which defines the outer boundaries of region 55. As shown in steps 2A and 2B, at one side of perimeter 58, the triangles of the one or more selected area(s) are filled with gray color, and at the other side of perimeter 58, the triangles of the one or more area(s) that were intentionally not selected by physician 30, are filled with white color. Note that perimeter 58 may be disconnected by one or more unselected area(s) that fall along one or more respective sections of the perimeter. In some embodiments, processor 42 is configured to estimate the path and shape of perimeter 58, e.g., by connecting sections of perimeter 58 between adjacent edges of selected area along the estimated path, or using any other suitable technique.

In some embodiments, at steps 2A and 2B, processor 42 is further configured to identify unselected areas 77a (shown in step 2A) and 77b (shown in step 2B) within selected region 55. Note that areas 77a and 77b were intended to be selected in the selection of region 55, so that in case processor 42 replaces the low-resolution selected areas 66a, 66b and 66c of region 55 with corresponding high-resolution areas of the same region, the unselected areas (e.g., areas 77a and 77b) will not be replaced, and therefore, will remain displayed in low resolution, which is undesired by physician 30 and may impair the geometrical quality of the anatomical map, and specifically in the present example, may also reduce the quality of the planned ablation.

Reference is now made to step 2A. In some embodiments, processor 42 is configured to identify that unselected area 77a comprises an isolated unselected area, which is surrounded by the one or more selected areas of region 55. In the present example, unselected area 77a is surrounded by selected area 66a. In such embodiments, processor 42 is configured to apply to unselected area 77a any suitable technique for selecting the triangles of unselected area 77a, also referred to herein as unselected triangles. Such techniques are described below, in a step 5 of FIG. 2.

In some embodiments, at step 5 processor 42 is configured to select the unselected triangles of area 77a, and to display these triangles filled with gray color, on display 46.

Reference is now made to step 2B. In some embodiments, processor 42 is configured to identify that selected areas 66b and 66c are at least partially disjoint from one another by unselected area 77b. Additionally or alternatively, processor 42 is configured to identify that unselected area 77b is partially enclosed by selected areas 66b and 66c.

In the example of step 2B, processor 42 is configured to identify that sections 70a and 70b also referred to herein as "openings" are separating between areas 66b and 66c.

Reference is now made to a step 3. In some embodiments, processor 42 is configured to compute the distance of a path between one or more pairs (typically between any pair) of the selected triangles located within areas 66b and 66c. In the context of the present disclosure and in the claims, the term "distance" refers to a distance measured on the surface of the anatomical map, which may be measured by the number of triangles (or another type of polygon) positioned along the path. The pair of the selected triangles may comprise one triangle from area 66b and one triangle from area 66c, or two triangles from the same area (e.g., from area 66b). Note that the path has, (i) at each side of the path, a selected triangle (e.g., selected from any of areas 66b and 66c) so as to produce connectivity between two selected areas, and (ii) one or more unselected triangles (e.g., from area 77b) located along the path that connects between the aforementioned selected triangles at each side of the path.

In some embodiments, processor 42 is further configured to select a path of unselected triangles of area 77b, between (i) a first triangle selected, by processor 42, from among the triangles of area 66b (that were selected by physician 30 at step 1), and (ii) a second triangle selected, by processor 42, from among the triangles of area 66c (also selected by physician 30 at step 1). In the example of step 3, processor 42 is configured to select a geodesic path 88a of triangles between the aforementioned first and second selected triangles of areas 66b and 66c, respectively.

In other embodiments, processor 42 is configured to select between areas 66b and 66c, any suitable path that is not a geodesic path, which comprises unselected triangles of area 77b.

In some embodiments, by producing geodesic path 88a, processor 42 is configured to divide area 77b into two unselected areas 77c and 77d. Note that area 77c is partially enclosed by areas 66b and 66c and by geodesic path 88a, but is still open by section 70a. Similarly, area 77d is partially enclosed by areas 66b and 66c and by geodesic path 88a, but is still open by section 70b.

At a step 4, using the techniques described in step 3 above, processor 42 is configured to surround all the unselected areas within region 55: (i) produce a geodesic path 88b of triangles for surrounding unselected area 77c, and (ii) produce a geodesic path 88c of triangles for surrounding the former unselected area 77c (shown in step 3).

In some embodiments, after producing geodesic paths 88b and 88c, processor 42 may produce a geodesic path 88d of triangles for dividing unselected area 77c into unselected areas 77e and 77f. Note that the formation of geodesic path 88d is not mandatory because after the formation of geodesic paths 88b and 88c, all the unselected areas of region 55 are surrounded, as also shown and described in the example of step 2A above.

In some embodiments, at step 5 processor 42 is configured to select the unselected triangles of the surrounded areas of region 55. In the example of step 5, region 55 comprises unselected area 77g, which is marked by a perimeter 78g and is surrounded by selected areas 66g and a geodesic path 88g of triangles.

In some embodiments, processor 42 is configured to apply to unselected area 77g, a flood fill algorithm for selecting the unselected triangles thereof. The flood fill algorithm is configured to select an unselected triangle within area 77g, and subsequently, to expand the selection of the unselected triangles in multiple directions shown by arrows 90, by selecting additional unselected triangles that are surrounding triangle 99.

In some embodiments, after selecting a triangle of area 77g that is adjacent to perimeter 78g, the flood fill algorithm continues to expand the selection in other directions 90 so as to select the remaining unselected triangles of area 77g. After selecting all the unselected triangles, processor 42 is configured to display, on display 46, the triangles of area 77g filled with gray color.

In some embodiments, processor 42 is configured to repeat the same above technique by applying the flood fill algorithm to other surrounded unselected areas of region 55, such as to area 77a shown in step 2A, and to areas 77c, 77e and 77f shown in step 4.

In other embodiments, instead of the flood fill algorithm, processor 42 is configured to apply to the unselected areas of region 55, any other suitable algorithm for selecting the unselected triangles of the surrounded unselected areas of region 55.

In some embodiments, after concluding step 5, processor 42 is configured to produce within perimeter 58, a revised selected region, comprising: (i) the areas selected by physician 30 in region 55 (e.g., areas 66a, 66b, 66c and 66g), and (ii) the unselected areas that were selected by processor 42 using, inter alia, the geodesic path formation and the flood fill algorithm as described in detail in steps 3-5 above.

In some embodiments, after concluding step 5, all the triangles of the revised selected region, which are located within the area surrounded by perimeter 58, are selected. In such embodiments, processor 42 is configured to replace the low mapping resolution of the region intended to be selected by physician 30, with high mapping resolution of the revised selected region described above. In alternative embodiments, the region intended to be selected may have high mapping resolution, so that processor 42 is configured to replace the high mapping resolution of the region intended to be selected by physician 30, with low mapping resolution of a revised selected region.

The embodiments described in the steps of FIG. 2 are provided by way of example, and the present invention is not limited to what has been particularly shown and described in the example embodiments of FIG. 2. In other embodiments, processor 42 is configured to apply any other suitable techniques, and any other suitable set of steps, for applying any suitable presentation to any regions of a map of heart 26 or any other organ of patient 28, which are selected either by processor 42 or by any user of system 20.

Figure 3:
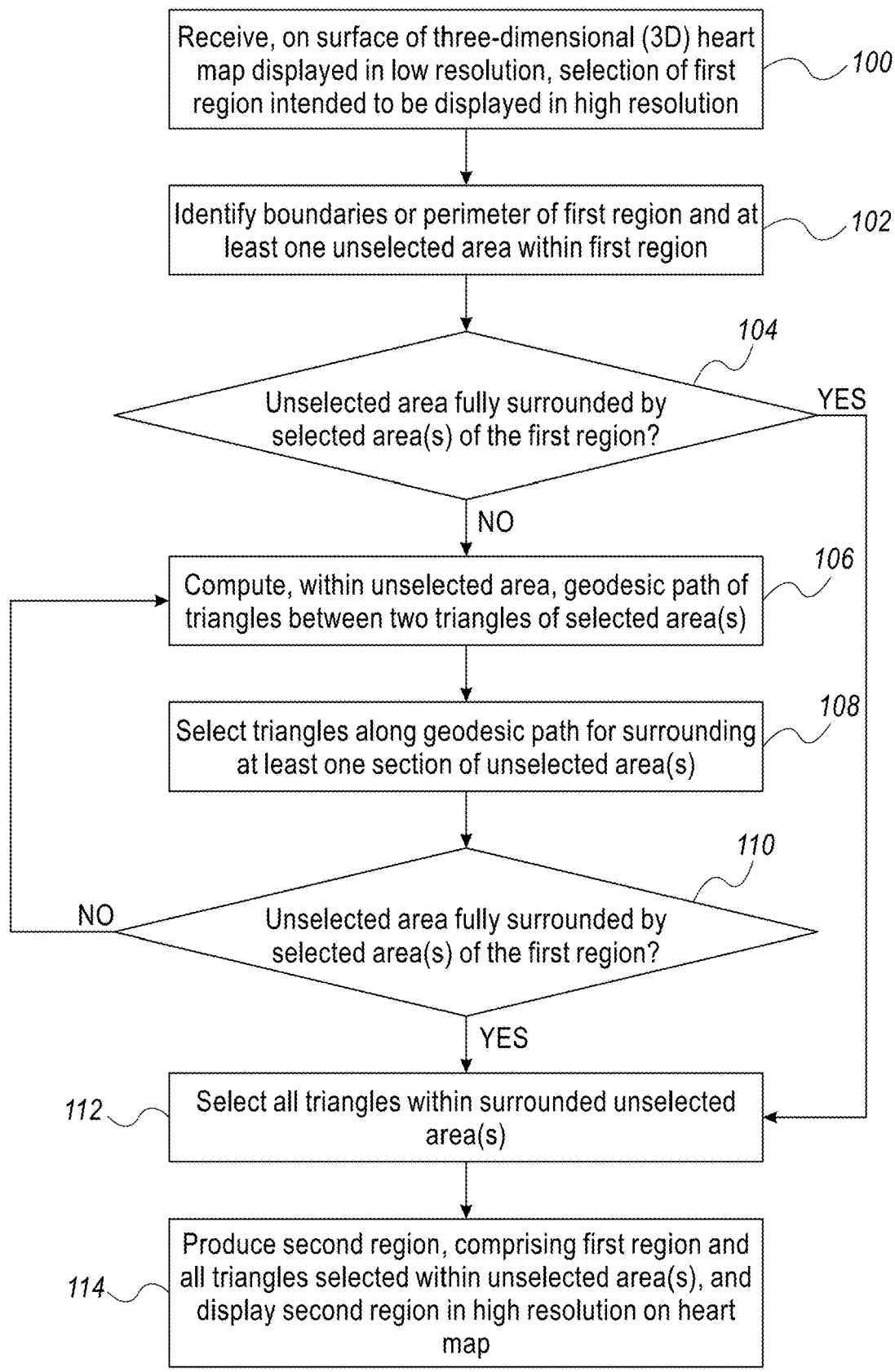
FIG. 3 is a flow chart that schematically illustrates a method for improving regional resolution in displaying anatomical mapping, in accordance with an exemplary embodiment of the present invention.

FIG. 3 is a flow chart that schematically illustrates a method for improving regional resolution in displaying the anatomical mapping of heart 26, in accordance with an embodiment of the present invention.

The method begins at a user selection step 100 with receiving from physician 30 or any other user of system 20, the selection of region 55. Region 55 may be selected by physician 30 using any suitable selection tool, such as the aforementioned brush of the CARTO™ system, as described in step 1 of FIG. 2 above. Note that at step 100, region 55 and the other sections of anatomical map 60, are displayed at low resolution (e.g., having the size of the triangle between about 10 mm and 30 mm) wherein after the selection, region 55 is intended to be displayed in higher resolution (e.g., having the size of the triangle between about 1 mm and 5 mm).

At a perimeter and unselected areas identification step 102, processor 42 identifies the boundaries of region 55, and one or more unselected areas (e.g., areas 77a and 77b) located within region 55. In the present example, the boundaries of region 55 are shown by perimeter 58, which is surrounding the user selection of region 55.

In some embodiments, processor 42 further identifies areas that were selected by the user within region 55, in the present example, area 66a (shown in step 1) and areas 66b and 66c (shown in step 2) of FIG. 2 above.

At a first decision step 104, processor 42 checks whether the unselected areas of region 55 are fully surrounded by the one or more selected areas of region 55. In the example shown in step 1 of FIG. 2 above, unselected area 77a is fully surrounded by selected area 66a. In other words, area 77a is "an island" surrounded by "the sea" of area 66a. In this example embodiment, the method proceeds to an island filling step 112, with all the triangles within the surrounded unselected area (e.g., area 77a) are selected by processor 42. The triangle selection of step 112 may be carried out using any suitable technique, such as applying the flood fill algorithm as described in detail in step 5 of FIG. 2 above.

In some embodiments, in case all the unselected areas, (by the user) within the surface defined by perimeter 58, have been selected by processor 42, the method proceeds to a revised resolution region production step 114. In the example shown in step 2A of FIG. 2 above, when all the triangles of areas 66a and 77a have been selected, the method proceeds to step 114.

In step 114, processor 42 removes region 55 and the areas selected by processor 42, which were intended to be initially selected by physician 30 in step 100 above. In some embodiments, processor 42 produces a revised region, which is substantially identical to the areas selected by physician (in step 100) and the areas selected by processor 42 in step 112 and in other steps of the method described below.

In some embodiments, the revised region has higher resolution compared to that of anatomical map 60, so that physician 30 can see more details, e.g., for planning an ablation procedure in this region, or for any other clinical need.

In other embodiments, at step 104, processor 42 may identify one or more unselected areas that are not surrounded by selected areas. For example, as shown in step 2B of FIG. 2 above, area 77b is partially surrounded by selected areas 66b and 66c.

In some cases, the partially surrounded unselected area may have two or more openings, such as sections 70a and 70b of area 77b shown in step 2B of FIG. 2 above. Such unselected areas are contiguous and are also referred to herein as "roads" passing between the selected areas (e.g., areas 66b and 76c). In other cases, the partially surrounded unselected area may have one opening, such as unselected area 77c, shown in step 3 of FIG. 2 above, and having section 70a. The geometric structure of area 77c is also referred to herein as "a peninsula."

In some embodiments, in step 104, when processor 42 identifies that one or more unselected areas within the surface defined by perimeter 58, are not surrounded by selected areas, the method proceeds to a geodesic path computation step 106.

At a step 108, as shown in step 3 of FIG. 2 above, processor 42 calculates the distance of paths between any selected triangles of areas 66b and 66c, and selects, between areas 66b and 66c, unselected triangles along geodesic path 88a, for surrounding at least one section of the unselected area. In case the unselected area has a "road" shape (e.g., area 77b), the geodesic path (e.g., geodesic path 88a) may block one opening of the unselected area. In case the unselected area has a "peninsula" shape (e.g., area 77c shown in step 3 of FIG. 2 above), the geodesic path (e.g., geodesic path 88b shown in step 4) may complete the circumference for surrounding the unselected area with one or more groups of selected triangles.

In some embodiments, in case of a peninsula-shaped unselected area, the triangles selected along the geodesic path are surrounding at least one section of unselected area.

At a second decision step 110, processor 42 checks whether the unselected areas of region 55 are fully surrounded as described above. In case at least one unselected area is not surrounded, the method loops back to step 106. For example, as shown in step 3 of FIG. 2 above, after selecting the triangles of geodesic path 88a, unselected area 77c is not fully surrounded by the selected triangles. In such embodiments, processor 42 applies steps 106 and 108 for producing geodesic path 88b, which blocks section 70a, and completes the circumference of area 77c with selected triangles, so as to surround area 77c.

In case, at step 110, all the unselected areas are surrounded by selected triangles, the method proceeds to step 112 for selecting all the triangles within the surrounded unselected areas, as described in detail in step 5 of FIG. 2 above.

Subsequently, at step 114 that concludes the method, the low mapping resolution of region 55 selected in step 100, is replaced with a region having the same surface mapped in high resolution, as described in detail above.

Note that after concluding step 114, display 46 displays (i) anatomical map 60 (which is of less interest for physician 30) in low resolution, and (ii) the area within the surface surrounded by perimeter 58, in high resolution, using any suitable resolution as described above.

This particular method of FIG. 3 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example sequence of steps, and the principles described herein may similarly be applied to other sorts of methods for presenting information in any suitable medical procedure.

Although the embodiments described herein mainly address anatomical mapping in planning of a cardiac ablation procedure, the methods and systems described herein can also be used in other applications, such as in any presentation of data and/or information used to carry out any medical procedure. Moreover, the methods and systems described herein can also be used in any application that includes manual selection and resolution improvement of a selected area.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for improving regional resolution in fast anatomical mapping, comprising:
   a processor, which is configured to:
      receive, on a surface of an anatomical map of a patient organ having a first presentation, a selection of a first selected region, which is intended to have a second presentation different from the first presentation, wherein the anatomical map comprises a mesh of polygons;
      identify (i) a perimeter of the first selected region comprising one or more selected areas, and (ii) at least an unselected area positioned within the first selected region; and
      identify, within the first selected region, at least an isolated unselected area surrounded by the one or more selected areas;
      select unselected polygons within the isolated unselected area;
      produce a second selected region, comprising (i) the first selected region, and (ii) the isolated unselected area; and
   an output device, which is configured to display the anatomical map having the second presentation applied to the second selected region.

2. The system according to claim 1, wherein the first presentation comprises a first mapping resolution of the anatomical map and the second presentation comprises a second mapping resolution of the second selected region of the anatomical map.

3. The system according to claim 1, wherein the processor is configured to select the unselected polygons by applying a flood fill algorithm to the unselected polygons within the isolated unselected area.

4. The system according to claim 1, wherein at least one of the polygons of the anatomical map comprises a triangle.

5. The system according to claim 1, wherein the first selected region comprises first and second selected areas at least partially disjoint from one another by the unselected area, wherein the processor is configured to identify the unselected area by identifying, within the first selected region, the unselected area that is partially enclosed by the first and second selected areas.

6. The system according to claim 5, wherein the anatomical map comprises a mesh of polygons, wherein the first selected area comprises first polygons and the second selected area comprises second polygons, wherein the first and second selected areas are at least partially disjoint by unselected polygons of the unselected area, and wherein the processor is configured to produce the second selected region by: (i) computing a distance between one or more pairs of the first and second polygons, and (ii) selecting a path of the unselected polygons located between any pair of the selected polygons, which is selected from the first and second polygons.

7. The system according to claim 6, wherein the path comprises a geodesic path.

8. The system according to claim 6, wherein at least one of the polygons comprises a triangle.

* * * * *